(12) United States Patent
Hsu et al.

(10) Patent No.: US 6,309,660 B1
(45) Date of Patent: Oct. 30, 2001

(54) UNIVERSAL BIOCOMPATIBLE COATING PLATFORM FOR MEDICAL DEVICES

(75) Inventors: Li-Chien Hsu, Mission Viejo; Can B. Hu; Sun-De Tong, both of Irvine, all of CA (US)

(73) Assignee: Edwards Lifesciences Corp., Irvine, CA (US)

( * ) Notice: Subject to any disclaimer, the term of this patent is extended or adjusted under 35 U.S.C. 154(b) by 0 days.

(21) Appl. No.: 09/362,468

(22) Filed: Jul. 28, 1999

(51) Int. Cl.$^7$ ............................ A61F 2/02; A61K 47/30; A01N 1/00
(52) U.S. Cl. ................ 424/425; 514/772.3; 523/112
(58) Field of Search ..................... 424/425; 514/772.3; 523/112

(56) References Cited

U.S. PATENT DOCUMENTS

| | | |
|---|---|---|
| 3,616,935 | 11/1971 | Love et al. . |
| 3,617,344 | 11/1971 | Leininger et al. . |
| 3,634,123 | 1/1972 | Eriksson et al. . |
| 3,717,502 | 2/1973 | Masuhara et al. . |
| 4,118,485 | 10/1978 | Eriksson et al. . |
| 4,229,838 | 10/1980 | Mano . |
| 4,565,740 | 1/1986 | Golander et al. . |
| 4,613,665 | 9/1986 | Larm . |
| 4,720,512 | 1/1988 | Hu et al. . |
| 4,786,556 | 11/1988 | Hu et al. . |
| 5,019,393 | 5/1991 | Ito et al. . |
| 5,049,403 | 9/1991 | Larm et al. . |
| 5,053,048 | 10/1991 | Pinchuk . |
| 5,132,108 | 7/1992 | Narayanan et al. . |
| 5,165,919 | 11/1992 | Sasaki et al. . |
| 5,270,046 | 12/1993 | Sakamoto et al. . |
| 5,308,641 | 5/1994 | Cahalan et al. . |
| 5,348,873 | 9/1994 | Matsuda et al. . |
| 5,417,969 | 5/1995 | Hsu et al. . |
| 5,510,418 | 4/1996 | Rhee et al. . |
| 5,532,311 | 7/1996 | Sirvio et al. . |
| 5,562,922 | 10/1996 | Lambert . |
| 5,563,056 | 10/1996 | Swan et al. . |
| 5,672,638 | 9/1997 | Verhoeven et al. . |
| 5,702,818 | 12/1997 | Cahalan et al. . |
| 5,811,151 | 9/1998 | Hendriks et al. . |
| 5,866,113 | 2/1999 | Hendriks et al. . |
| 5,874,500 | 2/1999 | Rhee et al. . |
| 5,879,697 | 3/1999 | Ding et al. . |
| 5,885,647 | 3/1999 | Larm et al. . |

FOREIGN PATENT DOCUMENTS

| | | |
|---|---|---|
| 55136064 | 10/1998 | (JP) . |
| 9618423 | 6/1996 | (WO) . |
| WO 96/37241 | 11/1996 | (WO) . |
| WO 97/29160 | 8/1997 | (WO) . |
| 9855128 | 12/1998 | (WO) . |

*Primary Examiner*—Carlos Azpuru
(74) *Attorney, Agent, or Firm*—Louis C. Cullman

(57) ABSTRACT

Universal, biocompatible coating platforms for articles intended to contact physiological fluids or tissues and associated methods of production are disclosed. The coating platforms of the present invention are composed of a polyelectrolyte molecular film containing one or more biologically active compounds. The molecular film is further complexed with the surface of an article by a crosslinked interpenetrating network (IPN) made from at least one multifunctional molecule and at least one crosslinking agent. The IPN may entrap additional biologically active compounds within the coating platform, or additional biologically active compounds may be bound to its outer surface. The coating platform of the present invention is ideally suited for providing medical devices with anti-thrombogenic coatings.

23 Claims, No Drawings

UNIVERSAL BIOCOMPATIBLE COATING PLATFORM FOR MEDICAL DEVICES

FIELD OF THE INVENTION

This invention relates to universal, biocompatible coating platforms for medical devices and methods for making same. More specifically, the present invention relates to universal, biocompatible coating platforms compatible with all materials commonly used to fabricate medical devices. In addition, the platforms of the present invention are capable of binding a vast variety of biologically active compounds to the medical device's surface without significantly impacting their activities.

BACKGROUND OF THE INVENTION

The ability of medical scientists to diagnose, treat and repair diseased and damaged tissues has increased dramatically in recent years. As new diagnostic and treatment devices are developed, medical scientists seek the optimum material for each application. The target anatomical site and intended use dictate the physical qualities demanded from candidate materials. Just as the human body has evolved into a variety of different tissue types, each perfectly adapted for its role, medical devices must be composed of equally specialized materials. For example, in vivo medical devices including catheters, cannuals and probes designed for insertion into narrow body structures such as the urethra, arteries, veins, and spinal column must have a minimal diameter, extreme flexibility, resilience and durability. Prosthetic medical devices such as artificial hips and joint replacements must be rigid and capable of surviving severe impact. Extracorpeal devices such as heart-lung machines and kidney dialysis equipment are complex mechanical devices that demand a diversity of functional and structural materials, each optimized for a particular function which may include contact with human tissues and body fluids.

In spite of the ongoing success of such devices, extracorpeal, in vivo, and prosthetic medical devices necessarily have surfaces that come into direct contact with blood and/or other body fluids and tissues, it is essential that the surfaces of these medical device be biocompatible. Thus, such biocompatible surfaces should not stimulate blood clotting (thrombogenesis), induce inflammatory or immune responses, kill or damage host tissues, or release toxic compounds when in contact with blood or living tissues. Of these biocompatibility issues, the most significant problem associated with the surfaces of materials commonly used to produce medical devices is their natural propensity to induce thrombogenesis. When this occurs on the surface of an implanted medical device, or within the chambers of an extracorpeal device, there is a potential risk of thromboembolism—the blocking of a blood vessel by a particle that has broken away from a blood clot—possibly resulting in a heart attack, lung failure, or stroke. Therefore, it has been, and continues to be, a primary focus of materials scientists and biomedical engineers to reduce or eliminate the thrombogenic potentials associated with the materials commonly used in medical device manufacturing.

At present, the most successful techniques known in the art for reducing thrombogenesis have evolved from the observation that certain compounds, when administered systemically, prevent blood clot formation. The most commonly used of these therapeutic anticoagulants is heparin, an acid mucopolysaccharide that acts in conjunction with naturally occurring antithrombin III to inhibit most of the serine proteases in the blood coagulation pathways. However, the use of systemic anticoagulants is not without risks. Heparin, for example, is metabolized through the liver and normally a single therapeutic dose will continue to inhibit blood clot formation in the patient for several hours. Should a traumatic event occur during the time systemic heparin is at therapeutic levels, the patent's ability to control bleeding will be impaired. Therefore, in an effort to reduce the sometimes potentially lethal side effects associated with systemic anticoagulants used in conjunction with medical devices, and to increase surface biocompatibility, materials scientists have experimented with heparin coatings that are intended to inhibit clot formation at its source, rather than systemically.

In addition to the continuing need to improve biocompatibility through reduced thrombogenesis associated with medical devices, there is a developing interest in using implantable or inter-dwelling medical devices as localized drug delivery vehicles as well. For example, the development of stenting techniques to treat cardiovascular disorders and to prevent restenosis (a closing, or narrowing of a previously opened lumenal space) has been on the rise. Typically, in such stenting applications, stents are made from non-reactive metals or polymers treated to have anti-thrombogenic surfaces and designed to mechanically support, or hold open, a body lumen such as a coronary artery. In spite of their initial success and promise, natural endothelial cell growth (normally lining the blood vessels) surrounding the stent site can be stimulated in response to injuries sustained during stent implantation. Consequently, endothelial cell over-growth itself may lead to neointimal hyperplasia thereby reducing or eliminating the stent's long term effectiveness. To reduce such cell growth and restenosis, early experiments are being conducted with anti-cell growth factors coupled to the stent's surface. Anti-thrombogenic agents and anti-cell growth factors are just two examples of biologically active compounds that materials scientists seek to bind to the surfaces of medical devices in order to improve their performance. Other equally important biologically active compounds that would be desirable to incorporate into medical devices include antibiotics, anti-inflammatory agents, lubricity-enhancing agents, hormones, and immune modulators, just to name a few.

Moreover, the materials that make up modern medical devices can be quite diverse. Examples of these structural and functional compounds include plastics and polymers such as polyethylene, polytetrafluoroethylene, silicone, silicone rubber, natural rubber, polyurethane, Dacron, gelatin-impregnated fluoropassivated Dacron, polyvinyl chloride, polystyrene, nylon, as well as natural rubber latex, stainless steel, other metals, ceramics and glass. Thus, the complexities normally associated with binding a single biologically active compound to the surface of a single material (homologous) device are significantly complicated when single or even multiple biologically active compounds are bound to the surface of a heterologous device (a device composed of more than one type of material, for example, an extracorpeal circuit having polyethylene channels with stainless steel couplers attached thereto).

There are two general methods known in the art for attaching biologically active compounds to such medical device surfaces. The first includes directly bonding the biologically active compound to the device's surface. The second involves indirectly bonding the biologically active compound to the device's surface through an intermediate layer. Each has its own benefits and drawbacks.

For example, providing a prior art medical device with a stable biologically active compound directly bound to its surface generally required the use of covalent chemical bonding techniques. For this to work the material used to make the medical device must possess chemical functional groups on its surface such as carbonyl carbons or primary amines which will form a strong, chemical bond with similar groups on the active compound. In the absence of such chemical bond forming functional groups, prior art techniques required activating the material's surface before coupling the biological compound. Surface activation is a process of generating, or producing, reactive chemical functional groups using harsh chemical or physical techniques. Such physical techniques include radio frequency plasma discharge, ionization, and heating. Similarly, harsh chemical prior art techniques for producing reactive functional groups include strong oxidizing acids, as well as solubalizing or etching with strong organic solvents.

As noted above, for these prior art techniques to work the biologically active compound itself must possess corresponding reactive functional groups which are chemically compatible with those on the medical device surface. Thus, biologically active compounds which did not possess such compatible functional groups needed to be chemically modified before they could be bound to the functional groups on the surface. For example, it is known that heparin can be modified to contain free terminal aldehyde groups through treating with nitrous acid. Alternatively, periodate oxidization could be used to generate chemically active aldehyde groups randomly dispersed throughout heparin's mucopolysaccharide chain. The modified heparin compounds thus formed could be covalently bound to an activated material surface possessing primary amines using a reductive amination process. As those skilled in the art will appreciate, these harsh physical and chemical treatments, in addition to the subsequent covalent bonding, can irreversibly inactivate the biologically active compounds.

An alternative prior art technique used to directly bond biologically active compounds to the surface of a medical device involved imbibing the biologically active compound into the surface with an organic solvent. In this process, a biologically active anion was co-precipitated with a cation surfactant then added to a mixture of organic solvent and the polymer material used to make the medical device. This mixture was then applied to the surface like paint. For example, heparin was mixed with dimethyl ammonium chloride surfactant, dioxane and polystyrene polymer. This mixture was then applied to the surface of a polystyrene medical device and allowed to dry. This produced a surface coated with polystyrene permeated with heparin.

In general, prior art methods used to increase the biocompatibility of medical devices by directly bonding biologically active compounds to their surface remain extremely limited in their utility, and lack versatility. For example, the known covalent coupling techniques require that a medical device be composed of a single reactive polymer, or a polymer susceptible to chemical or physical activation. Additionally, for these known techniques to work, the biologically active compounds selected for binding to the medical device's surface can not be susceptible to inactivation by either the harsh chemical modification techniques required to provide functionally active chemical binding sites or by the covalent bonding processes themselves. Moreover, many known medical devices were composed of materials that became brittle and lost their resiliency following surface activation. This rendered the resulting medical device virtually useless for applications requiring a flexible, resilient, or durable material.

Similarly, imbibing the biologically active compounds into the surface of a polymeric medical device was also limited. As known in the art, only charged biologically active compounds and medical devices composed of soluble polymers can be coated with such processes. Moreover, the solvents are generally toxic and difficult to handle. Also, the solvation process often made these devices brittle. A still further limitation in the utility of these known techniques is the continuing difficulty of obtaining an even application of the biologically active compound.

The known limitations of direct bonding techniques led to further attempts to develop a more versatile coating process. One resulting prior art technique involved indirectly bonding a biologically active compound to the device's surface through an intermediate layer. Intermediate layers may be either covalently bound to the surface, or bonded through strong inter-molecular electrostatic attractions such as Van der Waals forces. Examples of commonly used known intermediate layers include organic polymers such as silicones, polyamines, polystyrene, polyurethane, acrylates, and methoxysilanes.

Such an intermediate layer on the surface of a medical device provided the materials scientists with the beneficial flexibility of permitting the medical device's application to dictate the optimum manufacturing material, without being limited by surface coating compatibility considerations. The methods used to provide such known intermediate layers are diverse. They include coating the medical device in solvated polymer, covalent techniques for chemically bonding the intermediate layer to the device, and passive absorption techniques which rely on intermolecular forces to bind the intermediate layer to the medical device surface.

Further limiting the applicability of these techniques in the fact that metal and glass devices cannot have biocompatible compounds directly bonded to their surfaces. Therefore, it was necessary to coat metal and glass surfaces with solvated polymers such as polyurethane or polystyrene. Once coated with polymer, the metal or glass device could be further processed using techniques applied to medical devices made entirely from that polymer. However, since the coated medical devices exhibited the physical and chemical characteristics of the coating polymer, they were subject to the functional limitations associated with the coating polymer.

Covalent chemical bonding techniques for attaching an intermediate layer to the surface of a medical device are similar to those for directly chemically bonding biologically active compounds to the surface of the device. The materials used to fabricate the medical device must either contain chemically active functional groups on the device surface, or be susceptible to techniques for chemically activating the device's surface. Consequently, covalent chemical bonding techniques restrict the materials scientist to a limited number of materials from which to fabricate the medical device. Thus, the primary purpose for intermediate layers is correspondingly limited which significantly reduces their utility.

Passive absorption techniques of polymers such as polyamines and siloxanes can result in an intermediate layer on the surface of the medical device held in place through inter-molecular forces. Thus, the passively absorbed intermediate layer may be further stabilized by crosslinking their reactive groups using aldehydes. For example, polyethyleneimine is absorbed onto the surface of a medical device followed by crosslinking the chemical functional groups. Crosslinking is usually done using the alkene monoaldehyde, crotonaldehyde. While the crosslinking method may be effective in creating an intermediate layer on the surface of a medical device, it requires the use of highly toxic, extremely reactive, aldehyde crosslinking reagents.

The majority of the coating methods, including covalent chemical bonding and ionic chemical bonding techniques, were specifically developed to couple heparin to an intermediate layer on the surface of a medical device. Moreover, many of these prior art methods have been narrowly tailored for specific materials used to fabricate particular medical devices and include harsh physical or chemical modifications to these materials. This combination of specialized applications and harsh physical and chemical methods significantly restricted the versatility of these prior art coating methods. Moreover, many of these prior art methods were specifically designed to chemically bond heparin to the medical device. Consequently, the known methods for providing medical devices with biocompatible surfaces are highly specialized and lack universal application.

The heparin mucopolysaccharide chain possesses both carboxyl carbons and secondary amines that readily react with the chemical functional groups found on intermediate layers composed of polyamines or other polymeric substrates. Furthermore, heparin is a polyanion which readily forms insoluble ionic complexes with cationic surfactants such as polyethyleneimine. However, ionic complexes can be unstable and the heparin is known to leach off the surface of devices coated using insoluble ionic complexing techniques. When uncontrolled heparin leaching occurs, the medical device's biocompatibility is reduced increasing the risk of thrombogenesis. Moreover, it may not be desirable for the patient to receive the leached heparin systemically.

To overcome problems associated with heparin leaching, various methods have been developed to secure the ionic complex to the intermediate layer. One prior art technique uses an intermediate layer of polyethyleneimine, followed by a heparin coating which was stabilized using a second layer of polyethyleneimine. This method may be satisfactory for coupling heparin to the surface of a medical device. However, this process is limited to large polyanions (strong nucleophiles) that form insoluble complexes with the polyamine coating. Thus, this prior art technique is not useful in chemically bonding weak nucleophiles, electrophiles or uncharged molecules to the surface of a medical device. Consequently, this method has not proved to be versatile enough to provide biologically active coatings for the wide variety of new drug delivery vehicles.

Further complicating matters, there is a growing number of materials being used to fabricate medical devices and an increased use of extracorpeal and in vivo devices with heterologous surfaces. This, coupled with the recent interest in using in vivo devices as vehicles for drug delivery other than blood anticoagulants, has generated a significant demand for universal, biocompatible coating platforms for the surfaces of articles intended to contact physiological fluids and tissue.

Accordingly, it is an object of the present invention to provide universal, biocompatible coating platforms which can coat a variety of materials used to fabricate medical devices.

It is another object of the present invention to provide universal, biocompatible coating platforms that can coat medical devices with heterologous surfaces such as combinations of polymers, metal and glasses.

It is yet another object of the present invention to provide universal, biocompatible coating platforms that can be used to bind a variety of different biologically active molecules to the surface of medical devices while significantly retaining their biological activities.

SUMMARY OF THE INVENTION

These and other objects are achieved by the universal, biocompatible coating platforms and associated methods of the present invention which utilize water soluble biocompatible polymers ionically bound to other water soluble biocompatible polymers which form a molecular film (polyelectrolyte complex) on the surface of an article. The article's coated surface is then covered by a crosslinked, woven, net-like interpenetrating network (IPN) composed of at least one multifuntional, biocompatible polymer and a crosslinking agent. The universal, biocompatible coating platforms made in accordance with the teachings of the present invention are suitable for articles intended to contact physiological fluids and tissues. The universal, biocompatible coating platforms of the present invention provide surprisingly versatile, biocompatible surfaces that effectively bind a wide range of useful, biologically active compounds while retaining their activities.

In contrast to the prior art, the compositions and methods of the present invention can be used to provide universal, biocompatible coating platforms for the wide range of materials used to fabricate medical devices. Furthermore, the universal, biocompatible coating platforms made in accordance with the teachings of the present invention, in addition to coating single surfaces, are especially useful for providing heterologous substrates (articles made from more than one material) with an uniform surface that can serve as platforms for binding virtually all known biologically active compounds. Moreover, it should be emphasized, that the articles having the universal, biocompatible coating platforms of the present invention are non-toxic. Thus, they can be designed and utilized for both in vivo and extracorpeal applications.

For example, in one embodiment of the present invention, and without being bound to the following sequence of steps, universal, biocompatible coating platforms are provided by forming a thin layer of a water soluble high molecular weight cationic polymer on an article's surface. The surface is then treated with a water soluble anionic polymer instantly forming a stable, insoluble molecular film. A mixture of at least one multi-functional polymer, a crosslinking agent and another biologically active compound, if desired, is applied to the molecular film forming an IPN which physically entraps the biologically active compounds within a woven net-like configuration.

In another embodiment of the present invention, articles are provided with universal, biocompatible coating platforms as described above, wherein the multi-functional polymer which is applied to the molecular film is a polycation. The resulting IPN thus formed has a net positive charge and can be used to bind additional polyanions on its surface. Thus, universal, biocompatible coating platforms result composed of a molecular film complexed with a polyanion that is additionally stabilized by an IPN. This IPN forms a woven configuration entrapping other biologically active compounds within the weave. The surface of the IPN is also capable of supporting an additional polyanion layer.

The present invention also provides methods for producing universal biocompatible coating platforms having the steps of applying a water soluble, biocompatible polymer to the surface of an article, followed by rinsing the article in distilled water. A second water soluble, biocompatible polymer is then applied to the article's surface, followed by a second distilled water rinse. Next, a mixture of at least one multi-functional, biocompatible polymer and at least one crosslinking agent, and if desired, another biologically active compound, is applied to the article. The article is then rinsed a third time in distilled water and dried. It is understood that the rinse steps described herein are optional and are not limitations to the processes of the present invention.

In yet another embodiment of the present invention, a polypropylene hollow fiber blood oxygenator is the article which is provided with the universal, biocompatible coating platform.

Further objects and advantages of the universal, biocompatible, coating platforms produced in accordance with the teachings of the present invention, as well as a better understanding thereof, will be afforded to those skilled in the art from a consideration of the following detailed description of exemplary embodiments.

DETAILED DESCRIPTION OF EXEMPLARY EMBODIMENTS

The present invention provides universal, biocompatible coating platforms, and associated methods for their preparation, that can be used to impart a multitude of diverse beneficial physical and chemical properties to articles, specifically medical devices. The compositions and methods of the present invention can be used to provide virtually any type of material including, but not limited to, synthetic and natural polymers, metals, and glass, with stable, beneficial, universal, biocompatible coating platforms. In accordance with the teachings of the present invention, these novel, universal, biocompatible coating platforms can bind a variety of useful, biologically active compounds by either entrapping them within the weave of a crosslinked, woven, net-like interpenetrating network (IPN), or ionically complexing the biologically active compounds under, or on the surface of the IPN. Accordingly, this unique combination of beneficial properties provides materials scientists, biomedical engineers and medical researchers with compositions and techniques for altering the physical and chemical properties of medical devices and creating drug delivery mechanisms which were not previously available.

The universal, biocompatible coating platforms of the present invention have a water soluble polymer layer ionically bound with a second water soluble polymer forming an insoluble molecular film. This molecular film is an electrolyte complex which is further stabilized by the addition of a second layer containing a mixture of at least one multi-functional polymer (a polymer having two or more reactive groups), at least one crosslinking agent reactive with the multi-functional polymer(s), and optionally, one or more useful biologically active compound(s). The multi-functional polymer(s) and crosslinkers(s) of the second layer form an IPN that entraps all biologically active compound(s) added to the mixture and the polymers of the molecular film.

Many different articles made from a variety of materials will benefit from the compositions and methods of the present invention. Examples of articles that can be provided with the universal, biocompatible coating platforms of the present invention include, but are not limited to, contact lenses, ocular implants, catheters, medical tubing, cardiotomy reservoirs and heaters, extracorpeal blood circuits, heart valves, stents, pacemaker units, synthetic organs, artificial hips and joint prostheses. Non-limiting examples of materials used to fabricate these articles include silicones, rubbers, polyethers, polysulfones, polyamides, polyimides, polyurethanes, polycarbonates, polyesters, polyvinylhalides, polyacrylates, polyolefins, hydrogels, and derivatives, blends, copolymers, and multipolymers or combinations thereof. It is further contemplated as being within the scope of the present invention to provide universal, biocompatible coating platforms for composite surfaces, resins, metals, ceramics, glass and carbonaceous materials as well as a variety of other natural and/or synthetic materials.

The following non-binding theory is provided as an aid in understanding the chemical and physical properties unique to the present invention and is not intended as a limitation to its scope. The universal, biocompatible coating platforms of the present invention are multi-layered compositions that combine intermolecular and physical forces to create uniform biologically active coating platforms on the surfaces of articles, specifically medical devices. The formation of the universal, biocompatible coating platforms of the present invention begins with the application of a solvated polycation on to an article's surface. This polycation is initially held in place through molecular interactions such as Van der Waal forces. Immediately following the polycation application, the article is rinsed in water to remove unattached molecules. As a means of further stabilizing the polycation layer and providing additional biocompatibility to the surface, a polyanion solution is then applied. The reaction of the polycation and polyanion is immediate, and results in an insoluble polyelectrolyte complex precipitated on the surface of the article, forming a molecular film only a few angstroms, or less, thick. The net surface charge of the molecular film is controlled by the relative concentrations of the two electrolyte solutions. An excess of polycation results in a net positive charge, converesly, an excess of polyanions creates a negatively charged surface. For most applications, a net negative charge is preferred. It is understood that the rinse steps described herein are optional and are not limitations to the processes of the present invention.

Immediately following the formation of the molecular film, a mixture containing a polycation, a crosslinking agent reactive with the polycation, and additional biologically active compounds as desired, is applied to the article. The crosslinked polycation forms an IPN over the entire surface in a net like configuration. This crosslinked IPN entraps the molecular film and any biologically active compounds that were included in the mixture. The combination of intermolecular forces and the physical strength of the IPN combine to create a surprisingly stable and resilient coating platform that does not inactivate the biologically active compounds entrapped therein.

It is also possible to attach biologically active compounds to the IPN's surface through the positively charged residues of the crosslinked polycation. When a polyanion such as a mucopolysaccharide is attached to the IPN, insoluble complexes form on the outer layer of the medical device.

The polycations and polyanions used to form the molecular film and IPN are generally referred to as multi-functional molecules. The term multi-functional refers to a molecule with more than one reactive group, and thus is capable of forming complexes with adjacent multi-functional molecules.

The molecular weight of the multi-functional molecules of the present invention may range from between approximately 600 daltons to approximately 2,000,000 daltons, preferably in the range of between 10,000 daltons and 1,000,000 daltons, and more preferably between approximately 20,000 daltons to 30,000 daltons.

In addition to the molecular weight, it is useful to know the multi-functional molecule's equivalent weight when designing an IPN of the present invention. Equivalent weight, as defined herein, is determined by dividing the molecular weight of a multi-functional molecule by the number of functional groups present. The lower the equivalent weight for a given molecular weight, the greater the number of functional groups present in the molecule.

The chemical, physical and biological properties of the universal biocompatible coating platforms of the present invention can be modified to meet nearly any requirement, or combination of requirements. As previously disclosed, the attractive force and surface charge of the molecular film can be adjusted by controlling the relative polycation to polyanion concentrations.

Furthermore, the tightness of the IPN's "weave" can be controlled by adjusting the polycation to crosslinking reagent ratio and selecting a polycation and crosslinker with appropriate equivalent weights. For example, if it is desired to firmly secure a small biologically active compound to the surface of a medical device, a tight IPN weave can be created by using a higher proportion of crosslinking agent and a polycation or crosslinker with a low equivalent weight. If a drug delivery device is desired which requires the controlled release of a biologically active compound, a lower proportion of crosslinking reagent and polycation with a higher equivalent weight will result in a looser weave.

Examples of multi-functional polycations useful in the practice of the present invention include, but are not limited to, polyethyleneimine, polyacrylamide, polymers and copolymers of dimethylaminoethylmethacrylate and ammonio methacrylate. Similarly, multifunctional polyanions include, but are not limited to, dextran and dextran salts, cyclodextrans, chondroitin and chondroitin salts, chitosan, chitin derivatives, dermatan salts, starch and its derivatives, glcosaminoglycans, pectin, alginates, agar, gum, fructose, heparin and heparin salts.

Exemplary biologically active compounds that may be entrapped within the IPN of the present invention include, without limitation antibacterial agents, antiparasitic agents, antiviral agents, antifungal agents, amoebicidal agents, trichomonacidal agents, protease inhibitors, antihistamines, anti-inflammatory agents, anticholinergic agents, immunoglobulins, antigens, ophthalmic agents, chelating agents, immunosuppressive agents, antimetabolites, anesthetics, analgesic agents, antiarthritic agents, antiasthmatic agents, anticoagulants, antithrombogenic agents, anticonvulsants, antidepressants, antidiabetic agents, antineoplastics, antipsychotic agents, antihypertensive agents, muscle relaxants, proteins, peptides, hormones and lubricating agents.

As previously disclosed, the IPNs of the present invention are formed through the reaction of multi-functional molecules and crosslinking agents. Crosslinking agents couple, or form chemical bridges among, multi-functional molecules by chemical reactions which occur between the reactive groups on the crosslinking agent and multi-functional molecule. For example, crosslinking agents used in accordance with the present invention include, but are not limited to, epoxides, isocyanates, aldehydes and carboiimides.

Epoxide compounds and their derivatives are especially useful when used in accordance with the present invention. Epoxides contain a reactive oxirane ring (an epoxy group), a highly strained three-member ring consisting of two carbon atoms and one oxygen atom. Polyepoxides contain two or more oxirane rings and are thus capable of crosslinking two or more multi-functional molecules.

The epoxy groups react with a wide range of functional groups including, but not limited to, amino, carboxyl, and hydroxyl groups, making epoxides particularly useful with the multi-functional molecules of the present invention. Epoxide crosslinkers are also reactive with water, alcohols, phenols, organic acids and their salts, acid anhydrides, primary amines, secondary amines, tertiary amines, acetyls, acetylenes, alkyl halides, 2-aminothiols, ethyleneimine, ketones, phosphines, thiols, amides, acyl halides, azides, ammonia, carbon dioxide, benzene, sulfur dioxide, bismuth halide, carbon disulfide, silicon tetrahalide, and hydrogen sulfide, to name but a few.

Examples of useful polyepoxides include, without limitation, epichlorohydrin resins and glycidol derivatives such as glycidyl esters, glycidyl ethers and N-glycidyl compounds. Non-limiting examples include, polyglycidyl esters, diglycidyl butanediol ester, ethanediol diglycidyl ester, erythritol anhydride (EDE), butanediol diglycidyl ether (GAB), ethylene glycol diglycidyl ether, propylene glycol diglycidyl ether, glycerol-1,3-diglycidyl ether, polyethylene glycol diglycidyl ether, 1,6-hexanediol diglycidyl ether, propylene glycol diglycidyl ether, glycerol triglycidyl ether, diglycidyl, triglycidyl, and tetraglycidyl ethers and esters. Some specific examples of the foregoing include, without limitation, sorbitol polyglycidyl ether, polyglycerol polyglycidyl ether, pentaerythritol polyglycidyl ether, diglycerol polyglycidyl ether, triglycidyl tris (2-hydroxyethyl) isocyanurate, glycerol polyglycidyl ether, trimethylolpropane polyglycidyl ether, resorcinol diglycidyl ether, glycidyl ester ether of p-hydroxybenzoic acid, hydroquinone diglycidyl ether, neopentyl glycol diglycidyl ether, bisphenol A $(PO)_2$ diglycidyl ether, bisphenol S diglycidyl ether, hydrogenated bisphenol A diglycidyl ether, ethylene polyethylene glycol diglycidyl ether, propylene polypropylene glycol diglycidyl ether, polytetramethylene glycol diglycidyl ether, adipic acid diglycidyl ester, terephthalic acid diglycidyl ester, o-phthalic acid diglycidyl ester, and higher dicarboxylic acid diglycidyl esters, epichlorhydrin and mixtures thereof.

When the multi-functional molecule is polyvinyl alcohol, polyacrylic acid and/or polyacrylamide, croslinking agents such as isocyanates, aldehydes and carbodiimides are preferred. Examples of isocyanates used in accordance with the present invention include toluene diisocyanate, diphenylmethane diisocyanate, dicyclohexylmethane diisocyanate, and hexamethylene diisocyanate. Examples of carbodiimides and aldehydes useful as disclosed herein include dicyclohexylcarbodiimide, formaldehyde, and glutaraldehyde, to name but a few.

If the polyfunctional molecule comprises polyethyleneimine, then glycidyl derivatives are preferred crosslinking agents. Glycidol derivative compounds useful as disclosed herein are readily available from a variety of commercial sources. For example, a family of glycidol derivatives is available under the trade name Denacol® from Nagase Chemicals Ltd., Japan and includes mono-, di-, and tri-glycidyl ethers, glycidyl esters, and various N-glycidyl compounds (e.g. glycidyl phthalimide).

A variety of manufacturing techniques can be used to apply the universal, biocompatible coating platforms of the present invention to a medical device or article. For example, the medical device or article can be dipped into a solution containing the coating reagents of the present invention, the reagents can be atomized or sprayed onto the article's surface, or the reagents may be "painted" on the article using a suitable applicator. Those skilled in the art will realize these are but a few examples of techniques available for coating medical devices or articles. The exact method can be altered within the scope and teachings of the present invention and may depend on the nature of the surface to be coated and the physical make-up of the device. Catheters, blood oxygenators, contact lenses and the like can be dipped easily into a container of the coating reagents, whereas a complex extracorpeal circuit may require that the solutions be pumped through the device.

In an additional exemplary embodiment of the present invention, the device or article is immersed in a bath containing the polycation for a predetermined time ranging from about one second to several hours, or more. The exact exposure time will depend on the thickness of the coating desired, the type of surface being coated and other factors. Following the first dip, the article is dipped in distilled water, then dipped into solution of polyanion, then rinsed. The article is then dipped into a solution containing the IPN mixture and, if desired, a biologically active compound such as an antibiotic. After the final distilled water rinse, the article is allowed to dry and cure under ambient conditions. Alternatively, the drying and curing processes may be accelerated using gentle heating at temperatures between approximately 27° C. to about 100° C. In other exemplary embodiments the drying and curing temperature is between about 60° C. to 70° C., preferably 65° C. As those skilled in the art will realize, the exact optimum temperature for each application will vary, however, the range of temperatures used will most probably be between approximately room temperature and 150° C. As a general rule, the higher the temperature, the faster the drying and curing will occur. It is understood that the rinse steps described herein are optional and are not limitations to the processes of the present invention.

The solvent used to disperse the coating reagents will depend on the surface to be coated and the solubility of the coating reagent. For example, in one embodiment of the present invention polyethyleneimine is used to form the initial polycation layer. Polyethyleneimine is soluble in water and can be used as an aqueous solution (a compound dissolved in water) to coat a wettable, or hydrophilic, surface. However, if a non-wettable, or hydrophobic, surface like Teflon® is to be coated, it is useful to use water mixed with an organic solvent such as an alcohol.

As discussed above, the exact proportions of the various coating reagents to one another can vary depending upon the properties required for a particular application. However, it is anticipated that the molar ratio of crosslinker to multi-functional molecule in the present invention will range from 10:1 to 0.1:1 in most cases. Other molar ratios may apply within the scope and teachings of the present invention.

In addition to molar ratios, the absolute concentration of the coating reagents and the pH of the coating solutions may affect the characteristics of the present invention. In an exemplary embodiment of the present invention, the concentration of the multi-functional molecule (polyethyleneimine) ranges from approximately 0.1% to about 1.0% w/v. The crosslinking agent (glycidyl derivatives) ranges from approximately 0.1% to about 5.0% w/v. The coating solutions of the present invention may be applied across a wide range of pH. Generally, a neutral to slightly basic pH ranging from approximately 7 to about 12 is preferred. Other pH ranges are contemplated as being within the scope of the present invention.

The IPN of the universal, biocompatible, coating platforms made in accordance with the teachings of the present invention are extremely versatile. There are at least three distinct ways in which the biologically active compounds can be bound to, or within the IPN formed by the universal coatings of the present invention. Charged molecules and uncharged molecules of most any molecular weight can be entrapped within the weave of the IPN as disclosed above. Polyanions can be bound to the surface of the IPN resulting in an insoluble complex of polyanion and the IPN's charged molecules.

Both charged and uncharged molecules can be covalently bound to the surface of the IPN following aminating the entire IPN surface. For example, the polycation, polyethyleneimine (PEI), can be reduced with cyanoborohydride, or a similar reducing agent, converting imine groups on the surface of the PEI to secondary amines. The secondary amines thus formed can be coupled to a variety of functional groups commonly found on biologically active compounds such as, but not limited to, carbonyl carbons, aldehydes, ketones, hydroxyl groups, amines, and amides. Methods for reacting secondary amines to the aforementioned functional groups are known in the art.

A further understanding of the universal, biocompatible coating platforms and associated methods of the present invention will be afforded to those skilled in the art from the following non-limiting examples:

EXAMPLE 1

Formation of a Molecular Film (Polyelectrolyte Complex) on a Polymeric Surface

The optimum conditions for the formation a molecular film, or polyelectrolyte complex, made in accordance with the teachings of the present invention, were determined by treating 12.5 cm×8.5 cm sections of polypropylene microporous hollow fiber mats (PPmat). Separate sections of PPmat were treated with polyethyleneimine (PEI) solutions (0.05% wt/vol) in boronated buffer at various pHs or in water without pH adjustment. The PPmats were thoroughly rinsed with RO/DI water to remove excess PEI. Next, the PPmats were treated with a sodium heparin solution (0.1% wt/vol) in 0.15M NaCl, pH 3. One section of PPmat was treated using only the heparin solution as a control. After immersing the PPmats in sodium heparin solution for 5 min, the PPmats were rinsed thoroughly with RO/DI water to remove any unbound heparin.

The presence of heparin on the surface of the PEI demonstrated that a molecular film, or polyelectrolyte complex, had formed. Surface bound heparin was eluted using a high ionic strength salt solution which breaks down the polyelectrolyte complex. Sodium heparin, which is water soluble, dissolves in the high ionic strength salt solution; the PEI remains bound to the PPmat's surface due to Van der Waals force. Eluted heparin was quantified using factor Xa inhibition analysis. The amount of sodium heparin detected in the extraction solution correlates with the amount of heparin bound to the PPmat surface. The optimum molecular film, or polyelectrolyte complex, will have the highest concentration of heparin bound to the PPmat's surface.

TABLE 1

Sodium heparin concentration extracted from PPmat surfaces.

| Sample | Amount of Heparin Detected |
| --- | --- |
| PP mat, un-treated | 0 unit |
| PP mat exposed to heparin only | 0 unit |
| PP mat first exposed to PEI in pH = 8.8 | 8.1 unit |
| PP mat first exposed to PEI in water at pH = 7.1 | 1.4 unit |

The following solutions were prepared for use in the following Examples except as indicated.

Solution A: 0.05% (wt/vol) PEI in boric/borax buffer solution (pH=8.8)

Solution B: 0.5% chondroitin sulfate A (wt/vol) in 0.15N NaCl with pH adjusted

Solution C: a mixture of 0.05% PEI (wt/vol) (MW 25,000) and 0.5% (wt/vol) ethylene glycol diglycidol ether (EGDE) in boric/borax buffer Solution D: 0.5% (wt/vol) USP sodium heparin in 0.15 M NaCl, pH=3

Rinse Solution: Reverse osmosis (RO) or deionized (DI) water.

EXAMPLE 2

Formation of a Universal Biocompatible Coating Platform (Coating Platform) on the Surfaces of a Polypropylene Hollow Fiber Oxygenator A polypropylene hollow fiber oxygenator (oxygenator) was filled with Solution A, then drained. Next, the oxygenator was thoroughly rinsed with RO/DI water, then filled with Solution B, drained and rinsed as before. The oxygenator was then filled with Solution C and held at room temperature for thirty minutes before draining Solution C from the oxygenator and rinsing thoroughly with RO/DI water. The oxygenator was filled with Solution D, drained and thoroughly rinsed as before. The coated oxygenator was then dried in an oven at 140° F. for two hours.

The polypropylene hollow fiber oxygenator provided with a coating platform, made in accordance with the teachings of the present invention, was tested using an in vitro simulated extracorporeal circuit with freshly drawn human blood. The circuit consisted of a coated oxygenator, a reservoir, tubing and connectors. A control system utilizing an identical extracorpeal circuit with an untreated oxygenator was also employed. Freshly drawn, anticoagulant treated human blood was recirculated within the coated oxygenator circuit and the control circuit for 4 hours. Base-line levels (concentrations at the beginning of the experiment) of specific compounds selected as indicators of thrombogenic activation, and hence efficacy of the coating platform, were compared with levels of the same compounds after four hours of recirculation. Samples were also withdrawn from the oxygenator at predetermined intervals to quantify platelet activity.

The efficacy and stability of the coating platform of the present invention was assessed using four independent thrombogenic indicators. Coagulation activation was assessed by measuring plasma levels of the thrombin-antithrombin complex (TAT). Platelet factor IV levels were used to determine platelet activation. Elastase levels were measured to estimate leukocyte activation and total platelet and complete blood cell counts were used to assess platelet preservation and adhesion.

Specifically, thrombin-antithrombin levels are elevated when the coagulation pathway is activated. Blood recycled through a medical device such as an oxygenator that has no anti-thromboginic coating, such as the control device in this example, will have significantly elevated levels of TAT as compared to fresh human blood. An oxygenator provided with an antithrombogenic coating made in accordance with the teaching of the present invention will demonstrate lower TAT levels than the untreated control. Table 2, below, graphically illustrates this relationship demonstrating that the oxygenator coated in accordance with the teachings of the present invention possessed significant anti-thrombogenic activity.

Further, platelet factor four (PF4) is a heparin binding protein found in platelet α-granules that is released in response to ongoing platelet activation, a process consistent with thrombogenesis.

Therefore, increased levels of PF4 in the test sample, as compared to the control, indicates that the thrombogenic coating was inactive or unstable. In the present example, PF4 levels in the test sample were significantly lower than the control indicating that the anti-thrombogenic coating of the present invention reduced or prevented platelet activation.

Elastase is a peptidase enzyme released form polymorphonuclear (PMN) leukocytes (white blood cells) into the peripheral blood when the coagulation pathways are activated. The PMN elastase degrades coagulation proteins, thus modulating thrombotic and fibrolytic systems. Therefore, increased levels of PMN elastase signal blood coagulation activation which would indicate a breakdown in the anti-coagulates and/or associated coating platform. Table 2 shows that elastase levels in the treated blood oxygenator were significantly lower than the control indicating a stable, efficacious anti-thrombogenic coating platform.

Platelet adhesion is another excellent marker of thrombogenesis. Blood clot formation is often initiated when platelets adhere to the surface of a damaged vascular structure. Therefore, in environments where thrombogenic activity is activated are heightened, more platelets will move from the blood to the injured site. Table 3 demonstrates that a greater percentage of platelets are removed from the blood circulated through the uncoated device than the blood circulated through the oxygenator provided with an antithrombogenic coating in accordance with the teachings of the preset invention. The higher platelet levels in the treated oxygenator, as compared to the control, is consistent with a stable coating platform made in accordance with the teachings of the present invention.

TABLE 2

Percent increase from baseline levels after 4 hr. of blood circulation

|  | TAT | PF4 | PMN Elastase |
| --- | --- | --- | --- |
| Control | 504% | 100% | 910% |
| Test | 152% | 75% | 536% |

TABLE 3

Complete Blood Count Results

|  | HCT | RBC × $10^6$/ul | Plt × $10^3$/ul | Percent platelet depletion | WBC × $10^3$/ul |
| --- | --- | --- | --- | --- | --- |
| BASELINE CONTROL | 30.3 | 3.06 | 160 |  | 3.6 |
| 2' | 27.5 | 2.84 | 107 | 30 | 3.2 |
| 10' | 27.3 | 2.88 | 6 | 96 | 3.1 |
| 30' | 28.0 | 2.89 | 14 | 91 | 3.1 |
| 60' | 28.3 | 2.91 | 50 | 68 | 2.8 |
| 120' | 28.0 | 2.88 | 78 | 50 | 2.5 |
| 180' | 29.3 | 3.04 | 103 | 35 | 2.5 |
| 240' | 28.8 | 2.97 | 121 | 23 | 2.5 |
| TEST |  |  |  |  |  |
| 2' | 28.8 | 2.9 | 105 | 33 | 3.3 |
| 10' | 27.8 | 2.85 | 53 | 66 | 3.1 |
| 30' | 28.6 | 2.85 | 79 | 49 | 3.0 |
| 60' | 28.3 | 2.88 | 89 | 43 | 2.8 |
| 120' | 28.4 | 2.87 | 98 | 37 | 2.6 |
| 180' | 28.8 | 2.93 | 120 | 23 | 2.6 |
| 240' | 29.2 | 2.95 | 118 | 25 | 2.7 |

HCT = Hematocrit,
RBC = Red Blood Cell,
Plt = platelet,
WBC = White Blood Cell

Tables 2 and 3 graphically illustrate that thrombogenic indices are significantly lower in blood recirculated in the test circuit which was provided with an anti-thrombogenic coating made in accordance with the teaching of the present invention, when compared to blood recirculated in the control circuit which lacked an antithrombogenic coating. Similarly, the reduction in platelet counts during blood circulation is significantly less in the test circuit as compared to that in the control circuit (Table 3), indicating better platelet preservation and less platelet adhesion in the coated oxygenator.

EXAMPLES 3 AND 4

Two polypropylene hollow fiber oxygenators (oxygenator) were processed using the identical procedure described in Example 2 immediately above, except that a different Solution B was used in each Example. In Example 3, the dextran sulfate replaced the chondroitin sulfate and in Example 4, heparin sulfate was substituted for chondroitin sulfate. All other solutions and process steps remained the same.

The efficacy of these coating platforms made in accordance with the teaching for the present invention were evaluated using the same extracorporeal circuit described in Example 2. Platelet factor 4 (PF4), PMN elastase and platelet quantification were used to indicate thrombogenic activity. Table 4 demonstrates a lower PF4 activation and leukocyte activation (PMN elastase) and Table 5 shows improved platelet preservation in blood recirculated through the test circuit (treated) as compared to that in the control circuit (untreated).

TABLE 4

Percent increase from baseline levels after 4 hr. of blood circulation

|  | PF4 | PMN Elastase |
|---|---|---|
| Control | 113% | 404% |
| Test (DS) | 84% | 193% |
| Test (sodium heparin) | 47% | 513% |

DS = Dextran Sulfate

TABLE 5

Changes in hematocrit and platelet levels caused by recirculation

|  | HCT | Plt × 10^3/ul | Percent platelet depletion |
|---|---|---|---|
| BASELINE CONTROL | 37.9 | 181 |  |
| 2' | 33.6 | 122 | 27.9 |
| 10' | 35.1 | 23 | 86.7 |
| 30' | 34.1 | 36 | 79.2 |
| 60' | 34.6 | 68 | 60.4 |
| 120' | 35.5 | 106 | 39.2 |
| 180' | 35.4 | 129 | 25.9 |
| 240' | 36.4 | 144 | 18.5 |
| TEST (DS) |  |  |  |
| 2' | 35.7 | 146 | 16.5 |
| 10' | 34.1 | 101 | 40.8 |
| 30' | 34.9 | 129 | 25.3 |
| 60' | 35.0 | 134 | 22.5 |
| 120' | 34.5 | 142 | 17.3 |
| 180' | 36.7 | 145 | 18.3 |
| 240' | 37.1 | 151 | 15.5 |
| TEST (sodium heparin) |  |  |  |
| 2' | 32.2 | 156 | 4.5 |
| 10' | 32.4 | 151 | 7.5 |
| 30' | 32.3 | 151 | 7.1 |
| 60' | 31.3 | 153 | 7.8 |
| 120' | 31.6 | 159 | 2.1 |
| 180' | 32.1 | 160 | 2.0 |
| 240' | 32.3 | 160 | 2.8 |

HCT = Hematocrit, Plt = platelet

EXAMPLE 5

Coating of Oxygenators with PEI of Varying Molecular Weights

The effect of different molecular weight polyethyleneimine (PEI) polymers was assessed by varying the PEI used in Solution C. Two different molecular weights were selected. One oxygenator was treated with PEI with an average molecular weight (AMW) of 25,000 daltons and another with an AMW of 175,000 daltons. The coating procedure and all other solutions remained the same as those used in Example 2 above.

The coating platforms of the present invention were then tested to determine the effect different AMW PEIs had on anti-coagulate activity using the same extracorporeal circuit described in Example 2. Platelet factor 4 (PF4), PMN elastase and platelet quantification were used to indicate thrombogenic activity. Table 6 demonstrates a lower PF4 activation and leukocyte activation (PMN elastase) and Table 7 shows improved platelet preservation in blood recirculated through the test circuit (treated) as compared to that in the control circuit (untreated). Test results indicate that PEI of both AMWs are suitable for use in accordance with the teachings of the present invention and provide a stable, anti-thrombogenic biocompatible, coating platform.

TABLE 6

Percent increase from baseline levels after 4 hr. of blood circulation

|  | PF4 | PMN Elastase |
|---|---|---|
| Control | 537% | 1105% |
| Test (PEI with MW = 25,000) | 297% | 474% |
| Test (PEI with MW = 175,000) | 398% | 507% |

TABLE 7

Changes in hematocrit and platelet levels caused by recirculation

|  | HCT | Plt × 10^3/ul | Percent platelet depletion |
|---|---|---|---|
| BASELINE CONTROL | 33.3 | 168 |  |
| 2' | 29.2 | 98.8 | 41.2 |
| 10' | 30.1 | 32.5 | 80.7 |
| 30' | 30.1 | 32.5 | 80.7 |
| 60' | 30.6 | 64.5 | 61.6 |
| 120' | 30.7 | 102.9 | 38.8 |
| 180' | 30.6 | 110.3 | 34.4 |
| 240' | 31.5 | 118.1 | 29.7 |

TABLE 7-continued

Changes in hematocrit and platelet levels caused by recirculation

|  | HCT | Plt × 10^3/ul | Percent platelet depletion |
|---|---|---|---|
| TEST (MW 25,000) | | | |
| 2' | 29.3 | 106 | 36.9 |
| 10' | 28.6 | 86.7 | 48.4 |
| 30' | 28.4 | 98.8 | 41.2 |
| 60' | 29 | 117.1 | 30.3 |
| 120' | 29 | 127.7 | 24 |
| 180' | 29.3 | 129.3 | 23 |
| 240' | | | |
| TEST (MW 175,000) | | | |
| 2' | 30.9 | 122 | 27.2 |
| 10' | 31.3 | 99 | 41.1 |
| 30' | 31.3 | 108 | 35.6 |
| 60' | 31.9 | 122 | 27.1 |
| 120' | 31.9 | 130 | 22.8 |
| 180' | 31.8 | 133 | 20.9 |
| 240' | 32.2 | 134 | 20.1 |

EXAMPLE 6

A Biocompatible, Universal Coating Platform for an Oxygenator Containing Heparin and the Platelet Inhibitor, Reopro®, Incorporated into the IPN Made in Accordance with the Teachings of the Present Invention In addition to heparin, other bioactive substances can be incorporated into the coating platform's interpenetrating network (IPN) of the present invention to impart additional features or properties to an article's surfaces. In this example, a platelet surface IIb/IIIa receptor blocker, tradenamed Reopro®, (Eli Lilly and Company) was incorporated into the IPN. The coating procedure was the same as that described in the example 2, except that the 0.01 mg/ml Reopro® was added to solutions C and D.

The coating platforms of the present invention were then tested to determine the effect the added Reopro® had on anti-coagulate activity using the same extracorporeal circuit described in Example 2. Platelet factor 4 (PF4), PMN elastase and platelet quantification were used to indicate thrombogenic activity. Two oxygenators were each provided with the coating platform of the present invention. One coating platform had Reopro® incorporated into its IPN, the other did not. Both coating platforms were provided with heparin sulfate. As illustrated in Tables 8 and 9, the coating platform containing Reopro® demonstrated less PF4 activation and leukocyte activation (PMN elastase) and improved platelet preservation than the coating platform containing only heparin sulfate. Both oxygenators provided with anti-thrombogenic coating platforms were superior to the untreated control.

TABLE 8

Percent increase from baseline levels after 4 hr. of blood circulation

| | PF4 | PMN Elastase |
|---|---|---|
| Control | 325% | 975% |
| Test (with Reopro ®) | 160% | 442% |
| Test (Without Reopro ®) | 215% | 537% |

TABLE 9

Changes in hematocrit and platelet levels caused by recirculation

|  | HCT | Plt × 10^3/ul | Percent platelet depletion |
|---|---|---|---|
| BASELINE CONTROL | 32.3 | 202 | |
| 2' | 28.6 | 106 | 47.3 |
| 10' | 28.5 | 10.6 | 94.8 |
| 30' | 28.8 | 20 | 90.I |
| 60' | 28.4 | 70 | 64.9 |
| 120' | 29 | 105.9 | 47.6 |
| 180' | 29 | 131.1 | 35.1 |
| 240' | 29.3 | 148.3 | 26.6 |
| TEST (with Reopro ®) | | | |
| 2' | 29.3 | 170.2 | 15.7 |
| 10' | 28.8 | 130.4 | 35.4 |
| 30' | 29.2 | 126.5 | 37.4 |
| 60' | 29.5 | 130.2 | 35.6 |
| 120' | 29.2 | 134.9 | 33.2 |
| 180' | 30.2 | 141.4 | 30.0 |
| 240' | 29.4 | 149.1 | 26.2 |
| TEST (Without Reopro ®) | | | |
| 2' | 29.1 | 144.5 | 28.5 |
| 10' | 28.3 | 114.4 | 43.4 |
| 30' | 28.9 | 120.8 | 40.2 |
| 60' | 28.5 | 141.5 | 29.9 |
| 120' | 28.8 | 147.2 | 27.1 |
| 180' | 28.9 | 155.4 | 23.1 |
| 240' | 28.9 | 160.7 | 20.5 |

While this invention has been described with respect to various specific examples and embodiments, it is to be understood that the invention is not limited thereto and that it can be variously practiced within the scope of the following claims.

We claim:

1. A universal, biocompatible coating platform for the surface of an article intended to contact physiological fluids or tissues comprising:
   a molecular film having a first water soluble, biocompatible polymer ionically bound to a second water soluble, biocompatible polymer; and
   a crosslinked, interpenetrating network having at least one multi-functional, biocompatible polymer and at least one crosslinking agent covering said molecular film.

2. The universal, biocompatible coating platform of claim 1 further comprising a biocompatible, biologically active molecule ionically bound to surface of said crosslinked, interpenetrating network; said biologically active molecule selected from the group consisting of dextran and dextran salts, cyclodextrans, chondroitin and chondroitin salts, chitosan, chitin derivatives, dermatan salts, starch and its derivatives, glcosaminoglycans, pectin, alginates, agar, gum, fructose, heparin and heparin salts.

3. The universal, biocompatible coating platform of claim 1 wherein said crosslinked, interpenetrating network includes at least one biologically active compound.

4. The universal, biocompatible coating platform of claim 1 wherein said first water soluble, biocompatible polymer is a polycation selected from the group consisting of polyethyleneimine, polyacrylamide, polymers of dimethylaminoethylmethacrylate, polymers of ammonio methacrylate, and copolymers of dimethylaminoethylmethacrylate and ammonio methacrylate.

5. The universal, biocompatible coating platform of claim 1 wherein said second water soluble, biocompatible polymer is a polyanion selected from the group consisting of dextran, chondroitin and chondroitin salts, chitosan, chitin derivatives, dermatan salts, starch and its derivatives, glcosaminoglycans, pectin, alginates, agar, gum, fructose, heparin and heparin salts.

6. The universal, biocompatible coating platform of claim 1 wherein said at least one multi-functional, biocompatible polymer is a polycation selected from the group consisting of polyethyleneimine, polyacrylamide, polymers of dimethylaminoethylmethacrylate, polymers of ammonio methacrylate, and copolymers of dimethylaminoethylmethacrylate and ammonio methacrylate.

7. The universal, biocompatible coating platform of claim 1 wherein said at least one crosslinking agent is selected from the group consisting of epoxides, isocyanates, aldehydes, and carbodiimides.

8. The universal, biocompatible coating platform of claim 7, wherein said epoxide crosslinking agent is selected from the group consisting of epichlorohydrin resins, glycidol derivatives, glycidyl esters, glycidyl ethers, N-glycidyl compounds, polyglycidyl esters, diglycidyl butanediol ester, ethanediol diglycidyl ester, erythritol anhydride, butanediol diglycidyl ether, ethylene glycol diglycidyl ether, propylene glycol diglycidyl ether, glycerol-1,3-diglycidyl ether, polyethylene glycol diglycidyl ether, 1,6-hexanediol diglycidyl ether, propylene glycol diglycidyl ether, glycerol triglycidyl ether, diglycidyl, triglycidyl, tetraglycidyl ethers and esters, sorbitol polyglycidyl ether, polyglycerol polyglycidyl ether, pentaerythritol polyglycidyl ether, diglycerol polyglycidyl ether, triglycidyl tris (2-hydroxyethyl) isocyanurate, glycerol polyglycidyl ether, trimethylolpropane polyglycidyl ether, resorcinol diglycidyl ether, glycidyl ester ether of p-hydroxybenzoic acid, hydroquinone diglycidyl ether, neopentyl glycol diglycidyl ether, bisphenol A (PO)$_2$ diglycidyl ether, bisphenol S diglycidyl ether, hydrogenated bisphenol A diglycidyl ether, ethylene polyethylene glycol diglycidyl ether, propylene polypropylene glycol diglycidyl ether, polytetramethylene glycol diglycidyl ether, adipic acid diglycidyl ester, terephthalic acid diglycidyl ester, o-phthalic acid diglycidyl ester, and higher dicarboxylic acid diglycidyl esters, epichlorhydrin and mixtures thereof.

9. The universal, biocompatible coating platform of claim 7, wherein said isocyanate crosslinking agent is selected from the group consisting of toluene diisocyanate, diphenylmethane diisocyanate, dicyclohexylmethane diisocyanate, and hexamethylene diisocyanate.

10. The universal, biocompatible coating platform of claim 7, wherein said carbodoiimide crosslinking agent is dicyclohexylcarbodiimide.

11. The universal, biocompatible coating platform of claim 7, wherein said aldehyde crosslinking agent is selected from the group consisting of formaldehyde and glutaraldehyde.

12. The universal, biocompatible coating platform of claim 3, wherein said biocompatible, biologically active compound is selected from the group consisting of antibacterial agents, antiparasitic agents, antiviral agents, antifungal agents, amoebicidal agents, trichomonacidal agents, protease inhibitors, antihistamines, anti-inflammatory agents, anticholinergic agents, immunoglobulins, antigens, ophthalmic agents, chelating agents, immunosuppressive agents, antimetabolites, anesthetics, analgesic agents, antiarthritic agents, antiasthmatic agents, anticoagulants, antithrombogenic agents, anticonvulsants, antidepressants, antidiabetic agents, antineoplastics, antipsychotic agents, antihypertensive agents, muscle relaxants, proteins, peptides, hormones and lubricating agents.

13. A medical device intended to contact physiological fluids or tissue provided with the universal, biocompatible coating platform of claim 1.

14. A method for creating a universal, biocompatible coating platform on the surface of an article intended to contact physiological fluids or tissues, said method comprising the steps of:
   a) applying a first water soluble, biocompatible polymer to said surface of said article;
   b) applying a second water soluble, biocompatible polymer to said surface;
   c) applying a mixture of at least one multi-functional, biocompatible polymer and at least one crosslinking agent to said surface.

15. The method of claim 14 further comprising the additional step of adding a biocompatible, biologically active compound to said mixture of at least one multi-functional, biocompatible polymer and at least one crosslinking agent.

16. The method of claim 14 further comprising the additional step of applying a biocompatible, biologically active compound to said surface of said article after applying said mixture of at least one multi-functional, biocompatible polymer and at least one crosslinking agent.

17. The method of claim 14 wherein said first water soluble, biocompatible polymer is polycation selected from the group consisting of polyethyleneimine, polyacrylamide, polymers of dimethylaminoethylmethacrylate, polymers of ammonio methacrylate, and copolymers of dimethylaminoethylmethacrylate and ammonio methacrylate.

18. The method of claim 14 wherein said second water soluble, biocompatible polymer is a polyanion selected from the group consisting of dextran, chondroitin and chondroitin salts, chitosan, chitin derivatives, dermatan salts, starch and its derivatives, glcosaminoglycans, pectin, alginates, agar, gum, fructose, heparin and heparin salts.

19. The method of claim 14 wherein said at least one multi-functional, biocompatible polymer is a polycation selected from the group consisting of polyethyleneimine, polyacrylamide, polymers of dimethylaminoethylmethacrylate, polymers of ammonio methacrylate, and copolymers of dimethylaminoethylmethacrylate and ammonio methacrylate.

20. The method of claim 14 wherein said at least one crosslinking agent is a member selected from the group consisting of epoxides, isocyanates, aldehydes, and carbodiimides.

21. The method of claim 15 wherein said biocompatible, biologically active compound is selected from the group consisting of antibacterial agents, antiparasitic agents, antiviral agents, antifungal agents, amoebicidal agents, trichomonacidal agents, protease inhibitors, antihistamines, anti-inflammatory agents, anticholinergic agents, immunoglobulins, antigens, ophthalmic agents, chelating agents, immunosuppressive agents, antimetabolites, anesthetics, analgesic agents, antiarthritic agents, antiasthmatic agents, anticoagulants, antithrombogenic agents, anticonvulsants, antidepressants, antidiabetic agents, antineoplastics, antipsychotic agents, antihypertensive agents, muscle relaxants, proteins, peptides, hormones and lubricating agents.

22. The method of claim 16, wherein said biocompatible, biologically active compound is selected from the group consisting of dextran salts, chondroitin and chondroitin salts, chitosan, chitin derivatives, dermatan salts, starch and its derivatives, glcosaminoglycans, pectin, alginates, agar, gum, fructose, heparin and heparin salts.

23. A medical device intended to contact physiological fluids or tissues provided with the universal, biocompatible coating platform of claim 14.

* * * * *